US010583058B2

(12) United States Patent
Riley et al.

(10) Patent No.: US 10,583,058 B2
(45) Date of Patent: *Mar. 10, 2020

(54) PERSON SUPPORT APPARATUS HAVING PHYSIOLOGICAL SENSOR

(71) Applicant: Hill-Rom Services, Inc., Batesville, IN (US)

(72) Inventors: Carl W. Riley, Milan, IN (US); Timothy J. Receveur, Guilford, IN (US); David L. Ribble, Indianapolis, IN (US)

(73) Assignee: Hill-Rom Services, Inc., Batesville, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 16/149,400

(22) Filed: Oct. 2, 2018

(65) Prior Publication Data

US 2019/0029903 A1 Jan. 31, 2019

Related U.S. Application Data

(63) Continuation of application No. 15/673,760, filed on Aug. 10, 2017, now Pat. No. 10,111,794, which is a (Continued)

(51) Int. Cl.
*A61G 7/05* (2006.01)
*A61G 7/005* (2006.01)
(Continued)

(52) U.S. Cl.
CPC ............ *A61G 7/005* (2013.01); *A61B 5/024* (2013.01); *A61B 5/1115* (2013.01); (Continued)

(58) Field of Classification Search
CPC ......... A61B 5/00; A61B 5/024; A61B 5/0816; A61B 5/11; A61B 5/1101; A61B 5/1102; (Continued)

(56) References Cited

U.S. PATENT DOCUMENTS 2,194,809 A 3/1940 Powell, Jr.
3,325,799 A 6/1967 Farris
(Continued)

FOREIGN PATENT DOCUMENTS

EP 2 417 908 2/2012
EP 2 335 232 B1 8/2012
(Continued)

OTHER PUBLICATIONS

European search report from related EP 1- 17 6767 dated Jun. 30, 2011, 10 pages.

*Primary Examiner* — Van T Trieu
(74) *Attorney, Agent, or Firm* — Barnes & Thornburg LLP

(57) ABSTRACT

A person support apparatus includes a frame and a support surface cooperating with the frame to support a person. The person support apparatus also has a sensor coupled to one of the frame and the support surface. The sensor detects at least one characteristic associated with the person. A controller is coupled to the sensor. In response to at least one of a condition of the frame, a condition of the support surface, a position of the person, or a condition of the person, the controller operates to control the sensor by at least one of changing a gain of the sensor and changing a manner in which a signal from the sensor is filtered. In some instances, the controller turns the sensor off.

20 Claims, 11 Drawing Sheets

Related U.S. Application Data continuation of application No. 15/379,578, filed on Dec. 15, 2016, now Pat. No. 9,775,758, which is a continuation of application No. 14/686,244, filed on Apr. 14, 2015, now Pat. No. 9,549,675, which is a continuation of application No. 14/014,875, filed on Aug. 30, 2013, now Pat. No. 9,013,315, which is a continuation of application No. 12/881,252, filed on Sep. 14, 2010, now Pat. No. 8,525,679.

(60) Provisional application No. 61/243,714, filed on Sep. 18, 2009, provisional application No. 61/243,741, filed on Sep. 18, 2009, provisional application No. 61/243,806, filed on Sep. 18, 2009, provisional application No. 61/243,825, filed on Sep. 18, 2009.

(51) Int. Cl.
*A61B 5/11* (2006.01)
*A61B 5/024* (2006.01)

(52) U.S. Cl.
CPC ............ *A61B 5/1113* (2013.01); *A61B 5/1117* (2013.01); *A61B 5/1126* (2013.01)

(58) Field of Classification Search
CPC ... A61B 5/1107; A61B 5/1112; A61B 5/1113; A61B 5/1114; A61B 5/1115; A61B 5/1116; A61B 5/1118; A61B 5/1123; A61B 5/1126; A61G 7/00; A61G 7/002; A61G 7/012; A61G 7/05; A61G 7/0508; A61G 7/0509; A61G 7/05792
See application file for complete search history.

(56) References Cited

U.S. PATENT DOCUMENTS

| | | |
|---|---|---|
| 3,631,438 A | 12/1971 | Lewin |
| 3,644,950 A | 2/1972 | Lindsay, Jr. |
| 3,727,606 A | 4/1973 | Sielaff |
| 3,836,900 A | 9/1974 | Mansfield |
| 3,996,928 A | 12/1976 | Marx |
| 4,146,885 A | 3/1979 | Lawson, Jr. |
| 4,195,287 A | 3/1980 | McCoy et al. |
| 4,245,651 A | 1/1981 | Frost |
| 4,422,458 A | 12/1983 | Kravath |
| 4,481,686 A | 11/1984 | Lacoste |
| 4,483,029 A | 11/1984 | Paul |
| 4,485,505 A | 12/1984 | Paul |
| 4,525,885 A | 7/1985 | Hunt et al. |
| 4,559,656 A | 12/1985 | Foster |
| 4,564,965 A | 1/1986 | Goodwin |
| 4,595,023 A | 6/1986 | Bonnet |
| 4,602,643 A | 7/1986 | Dietz |
| 4,637,083 A | 1/1987 | Goodwin |
| 4,657,026 A | 4/1987 | Tagg |
| 4,677,857 A | 7/1987 | Feldmann |
| 4,681,098 A | 7/1987 | Lee |
| 4,694,520 A | 9/1987 | Paul et al. |
| 4,757,825 A | 7/1988 | Diamond |
| 4,799,276 A | 1/1989 | Kadish |
| 4,838,309 A | 6/1989 | Goodwin |
| 4,889,131 A | 12/1989 | Salem et al. |
| 4,907,845 A | 3/1990 | Wood |
| 4,934,468 A | 6/1990 | Koerber, Sr. et al. |
| 4,935,968 A | 6/1990 | Hunt et al. |
| 4,942,635 A | 7/1990 | Hargest et al. |
| 4,949,412 A | 8/1990 | Goode |
| 4,949,414 A | 8/1990 | Thomas et al. |
| 4,971,065 A | 11/1990 | Pearce |
| 5,010,772 A | 4/1991 | Bourland et al. |
| 5,052,067 A | 10/1991 | Thomas et al. |
| 5,057,819 A | 10/1991 | Valenti |
| 5,060,174 A | 10/1991 | Gross |
| 5,101,828 A | 4/1992 | Welkowitz et al. |
| 5,117,518 A | 6/1992 | Schild |
| 5,170,364 A | 12/1992 | Gross et al. |
| 5,182,826 A | 2/1993 | Thomas et al. |
| 5,184,112 A | 2/1993 | Gusakov |
| 5,276,432 A | 1/1994 | Travis |
| 5,283,735 A | 2/1994 | Gross et al. |
| 5,539,942 A | 7/1996 | Melou |
| 5,588,167 A | 12/1996 | Pahmo et al. |
| 5,664,270 A | 9/1997 | Bell et al. |
| 5,794,288 A | 8/1998 | Soltani et al. |
| 5,796,059 A | 8/1998 | Boon |
| 5,815,864 A | 10/1998 | Sloop |
| 5,817,146 A | 10/1998 | Augustine |
| 5,829,081 A | 11/1998 | Pearce |
| 5,873,137 A | 2/1999 | Yavets-Chen |
| 5,934,280 A | 8/1999 | Viard et al. |
| 5,964,720 A | 10/1999 | Pelz |
| 5,970,789 A | 10/1999 | Meyer et al. |
| 6,009,580 A | 1/2000 | Caminade et al. |
| 6,011,477 A | 1/2000 | Teodorescu et al. |
| 6,034,526 A | 3/2000 | Montant et al. |
| 6,067,019 A | 5/2000 | Scott |
| 6,079,068 A | 6/2000 | Viard |
| 6,094,762 A | 8/2000 | Viard et al. |
| 6,208,250 B1 | 3/2001 | Dixon et al. |
| 6,212,718 B1 | 4/2001 | Stolpmann et al. |
| 6,386,051 B1 | 5/2002 | Yoshimi et al. |
| 6,493,568 B1 | 12/2002 | Bell et al. |
| 6,560,804 B2 | 5/2003 | Wise et al. |
| 6,721,980 B1 | 4/2004 | Price et al. |
| 6,739,006 B2 | 5/2004 | Borders et al. |
| 6,813,790 B2 | 11/2004 | Flick et al. |
| 6,984,207 B1 | 1/2006 | Sullivan et al. |
| 7,077,810 B2 | 7/2006 | Lange et al. |
| 7,127,948 B2 | 10/2006 | Tavares et al. |
| 7,183,930 B2 | 2/2007 | Basir et al. |
| 7,242,306 B2 | 7/2007 | Wildman et al. |
| 7,245,956 B2 | 7/2007 | Matthews et al. |
| 7,248,933 B2 | 7/2007 | Wildman |
| 7,253,366 B2 | 8/2007 | Bhai |
| 7,296,312 B2 | 11/2007 | Menkedick et al. |
| 7,304,580 B2 | 12/2007 | Sullivan et al. |
| 7,306,564 B2 | 12/2007 | Nakatani et al. |
| 7,314,451 B2 | 1/2008 | Halperin et al. |
| 7,315,535 B2 | 1/2008 | Schuman |
| 7,316,171 B2 | 1/2008 | Nemoto |
| 7,319,386 B2 | 1/2008 | Collilns, Jr. et al. |
| 7,330,127 B2 | 2/2008 | Price et al. |
| 7,459,645 B2 | 12/2008 | Skinner et al. |
| 7,472,439 B2 | 1/2009 | Lemire et al. |
| 7,513,163 B2 | 4/2009 | Fukutomi et al. |
| 7,515,059 B2 | 4/2009 | Price et al. |
| 7,629,890 B2 | 12/2009 | Sullivan et al. |
| 7,656,299 B2 | 2/2010 | Gentry et al. |
| 7,714,238 B2 | 5/2010 | Skinner et al. |
| 7,926,131 B2 | 4/2011 | Menkedick et al. |
| 8,159,214 B2 | 4/2012 | Uchiyama et al. |
| 8,258,963 B2 | 9/2012 | Dixon et al. |
| 8,281,433 B2 | 10/2012 | Riley et al. |
| 8,525,679 B2 | 9/2013 | Riley et al. |
| 8,525,680 B2 | 9/2013 | Riley et al. |
| 8,525,682 B2 | 9/2013 | Dixon et al. |
| 8,752,220 B2 | 6/2014 | Soderberg et al. |
| 9,013,315 B2 | 4/2015 | Riley et al. |
| 9,549,675 B2 | 1/2017 | Riley et al. |
| 9,775,758 B2 | 10/2017 | Riley et al. |
| 10,111,794 B2 | 10/2018 | Riley et al. |
| 2001/0001235 A1 | 5/2001 | Menkedick et al. |
| 2001/0004778 A1 | 6/2001 | Heimbrock et al. |
| 2004/0111045 A1 | 6/2004 | Sullivan et al. |
| 2005/0027416 A1 | 2/2005 | Basir et al. |
| 2005/0168341 A1 | 8/2005 | Reeder et al. |
| 2005/0190062 A1 | 9/2005 | Sullivan et al. |
| 2005/0190068 A1 | 9/2005 | Gentry et al. |
| 2006/0101581 A1 | 5/2006 | Blanchard et al. |
| 2006/0179952 A1 | 8/2006 | Tavares et al. |
| 2007/0083125 A1 | 4/2007 | Ouchi et al. |
| 2007/0118054 A1 | 5/2007 | Pinhas et al. |

(56) References Cited

U.S. PATENT DOCUMENTS

| | | |
|---|---|---|
| 2007/0272450 A1 | 11/2007 | Skinner et al. |
| 2008/0010748 A1 | 1/2008 | Menkedick et al. |
| 2008/0039736 A1 | 2/2008 | Nemoto |
| 2008/0060138 A1 | 3/2008 | Price et al. |
| 2008/0114260 A1 | 5/2008 | Lange et al. |
| 2008/0169931 A1 | 7/2008 | Gentry et al. |
| 2008/0269625 A1 | 10/2008 | Halperin et al. |
| 2008/0275349 A1 | 11/2008 | Halperin et al. |
| 2011/0234408 A1 | 9/2011 | Dixon et al. |
| 2014/0002267 A1 | 1/2014 | Riley et al. |
| 2015/0216451 A1 | 8/2015 | Riley et al. |
| 2017/0095162 A1 | 4/2017 | Riley et al. |
| 2017/0333274 A1 | 11/2017 | Riley et al. |

FOREIGN PATENT DOCUMENTS

| | | |
|---|---|---|
| JP | 06315424 A2 | 11/1994 |
| WO | WO 86/05965 | 10/1986 |
| WO | WO 2004/045407 | 6/2004 |
| WO | WO 2008/153912 | 12/2008 |

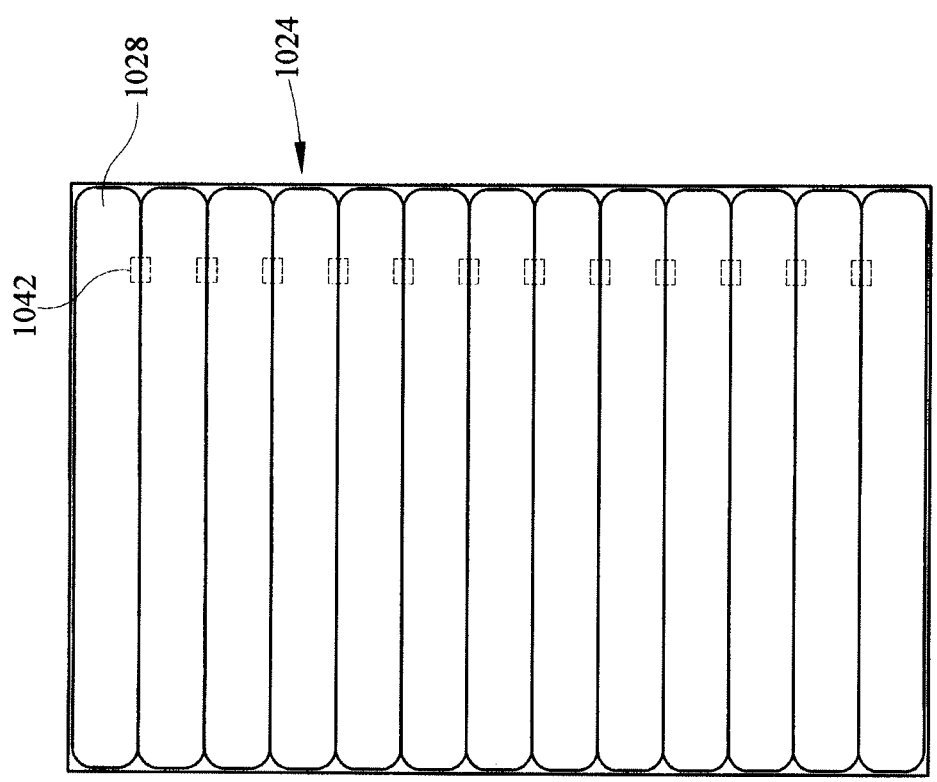

PERSON SUPPORT APPARATUS HAVING PHYSIOLOGICAL SENSOR

CROSS-REFERENCE TO RELATED APPLICATIONS

This application is a continuation of U.S. application Ser. No. 15/673,760, filed Aug. 10, 2017, now U.S. Pat. No. 10,111,794, which is a continuation of U.S. application Ser. No. 15/379,578, filed Dec. 15, 2016, now U.S. Pat. No. 9,775,758, which is a continuation of U.S. application Ser. No. 14/686,244, filed Apr. 14, 2015, now U.S. Pat. No. 9,549,675, which is a continuation of U.S. application Ser. No. 14/014,875, filed Aug. 30, 2013, issued as U.S. Pat. No. 9,013,315 on Apr. 21, 2015, which is a continuation of U.S. application Ser. No. 12/881,252, filed Sep. 14, 2010, issued as U.S. Pat. No. 8,525,679 on Sep. 3, 2013, which claims the benefit, under 35 U.S.C. § 119(e), of U.S. Provisional Application Nos. 61/243,714; 61/243,741; 61/243,806; and 61/243,825; each of which was filed Sep. 18, 2009 and each of which is hereby incorporated by reference herein.

The present application relates to U.S. application Ser. No. 12/881,285, filed Sep. 14, 2010, issued as U.S. Pat. No. 8,525,680 on Sep. 3, 2013, and titled "Apparatuses for Supporting and Monitoring a Condition of a Person."

BACKGROUND

This disclosure relates to person support apparatuses such as hospital beds. More particularly, the present disclosure relates to person support apparatuses having sensors that sense one or more conditions of the person or of the apparatus.

Person support apparatuses include beds, chairs, stretchers, seats, mattresses, therapy surfaces, furniture, and the like, or other apparatuses that support a person. Hospital beds and stretchers, hospital mattresses, and wheelchairs are examples of such apparatuses that support persons. Consumer beds, chairs, and furniture are also examples of such person support apparatuses, as are seats for vehicles, businesses, and venues.

Vital signs monitors monitor one or more physiological parameters of a person, such as body temperature, pulse rate, heart rate, blood pressure, and respiratory rate, as well as other body signs, such as end-tidal CO2, SpO2 (saturation of oxygen in arterial blood flow), and other indicators of the person's physiological state. Position and movement detection systems monitor the position and/or movement of a person to determine if they are attempting to exit the support apparatus.

While various person support apparatuses have been developed, there is still room for development. Thus, a need persists for further contributions in this area of technology.

SUMMARY

The present disclosure includes one or more of the features recited in the appended claims and/or the following features which, alone or in any combination, may comprise patentable subject matter.

A person support apparatus may include a frame and a support surface cooperating with the frame to support a person. The person support apparatus may also have a sensor coupled to one of the frame and the support surface, the sensor detecting at least one characteristic associated with the person. A controller may be coupled to the sensor. In response to at least one of a condition of the frame, a condition of the support surface, a position of the person, or a condition of the person, the controller may operate to control the sensor by at least one of changing a gain of the sensor and changing a manner in which a signal from the sensor is filtered.

The controller may also be operable to turn the sensor on and off. The sensor may include a plurality of sensors and the controller may operate to control each of the plurality of sensors by at least one of changing a gain of each of the plurality of sensors and changing a manner in which signals from each of the plurality of sensors is filtered. The controller may operate to turn off some of the plurality of sensors and to turn on others of the plurality of sensors. The determination by the controller as to which sensors may be turned off and which sensors may be turned on may be based on a position of the person relative to the support surface or relative to the frame. Alternatively or additionally, the determination by the controller as to which sensors may be turned off and which sensors may be turned on may be based on movement of a first portion of the frame relative to a second portion of the frame.

The controller may be operable to implement via software at least one of a high pass filter, a low pass filter, and a band pass filter and/or the controller may be operable to selectively switch the sensor between being coupled to a high pass filter, a low pass filter, and a band pass filter. The controller may be operable to filter out noise associated with at least one of a first electric component associated with the support surface and a second electric component associated with the frame. The controller may be operable to filter out noise associated with separate medical equipment in a person's room based on information received from an electronic medical record (EMR) system.

The sensor may comprise a force sensing load cell coupled to the frame or a pressure sensing strip coupled to the support surface or both. The support surface may comprise a mattress that may have inflatable bladders and the sensor may include a pressure sensor that measures pressure in at least one of the bladders. The sensor may sense at least one of the person's weight, heart rate, respiration rate, and temperature. The at least one characteristic associated with the person and sensed by the sensor my include at least one of a force profile, a pressure in a bladder, and a physiological characteristic.

The controller may adjust the gain of the sensor as a function of a difference between a first position of the person relative to one of the frame and the support surface and a second position of the person relative to one of the frame and the support surface. The controller may be operable to prevent a user from accessing predetermined functions of the person support apparatus based on at least one of signal strength and clarity of a signal from the sensor.

The sensor may include a plurality of sensors and the controller may control the gain of each of the plurality of sensors such that signal strength of an output signal of each of the plurality of sensors may be substantially equal. The sensor may include a first sensor and a second sensor and the controller may operate to amplify a signal from the first sensor when signal strength of the signal from the first sensor is less than that of the second sensor. Alternatively or additionally, a signal from the first sensor may be filtered when signal clarity of the signal from the first sensor is less than that of the second sensor.

According to the present disclosure a system may be configured to select between a first sensor and a second sensor based on at least one of the position of a person on a person support surface, the pressure in support surface fluid bladders, a difference between the signal strength and/or clarity of the first sensor and a signal strength and/or clarity of a second sensor, and person support apparatus status information. Also according to the present disclosure, a system may be configured to amplify and/or filter a signal from a first sensor as a function of at least one of a difference between the signal strength and/or clarity of the first sensor and a signal strength and/or clarity of a second sensor, the position of a person on a person support surface, the pressure in support surface fluid bladders, a comparison between a first sensor and second sensor, and person support apparatus status information.

Additional features alone or in combination with any other feature(s), including those listed above and those listed in the claims and those described in detail below, may comprise patentable subject matter. Others will become apparent to those skilled in the art upon consideration of the following detailed description of illustrative embodiments exemplifying the best mode of carrying out the invention as presently perceived.

BRIEF DESCRIPTION OF THE DRAWINGS

Referring now to the illustrative examples in the drawings, wherein like numerals represent the same or similar elements throughout:

FIG. 8 is a top view of the fluid bladders within the person support surface of FIG. 2 with pressure sensors integrated in the bladders according to yet another illustrative embodiment;

DETAILED DESCRIPTION

Figure 1:
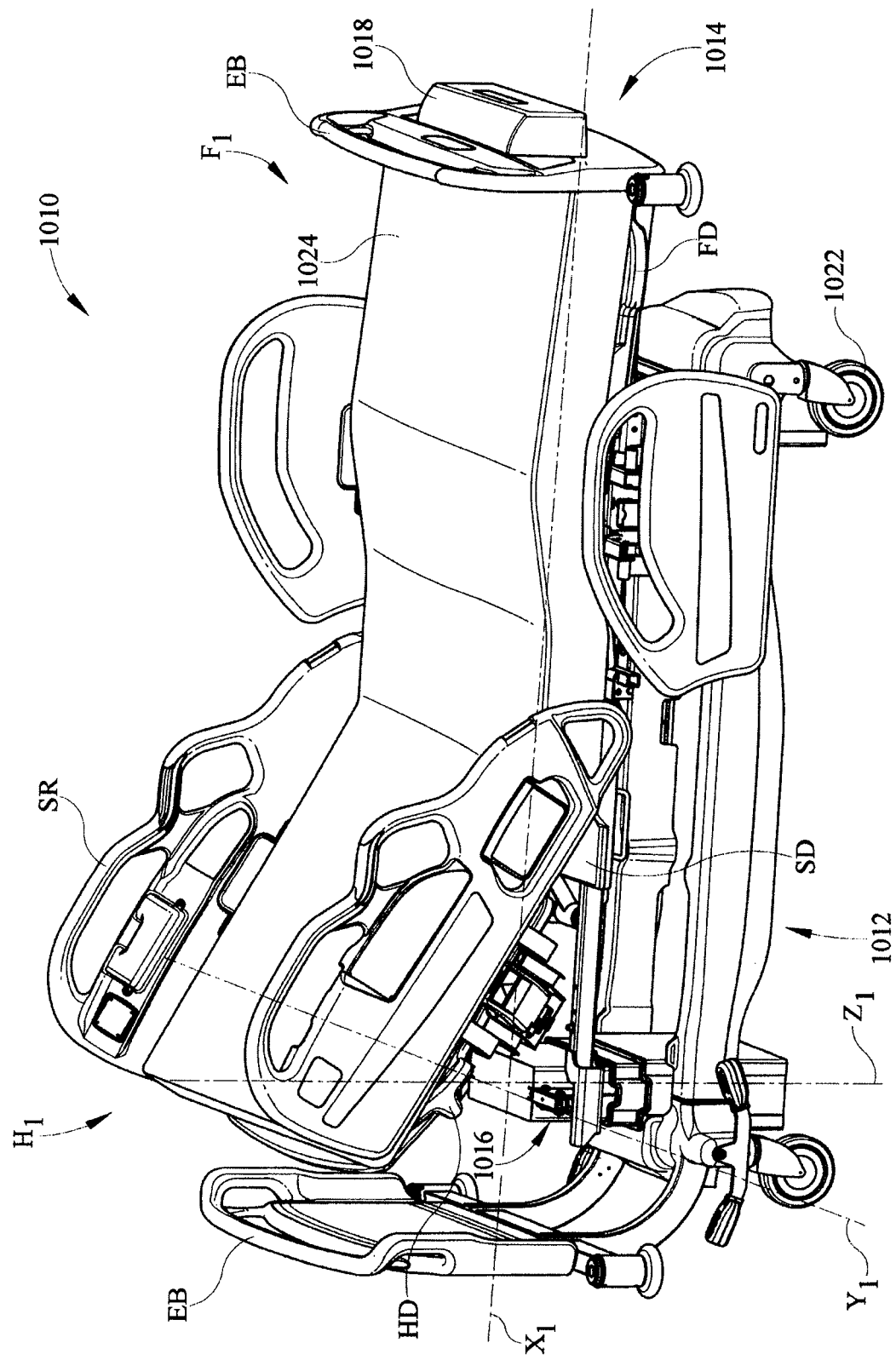
FIG. 1 is a perspective view of an embodiment of a person support apparatus according to one illustrative embodiment.

While the present disclosure can take many different forms, for the purpose of promoting an understanding of the principles of the disclosure, reference will now be made to the embodiments illustrated in the drawings, and specific language will be used to describe the same. No limitation of the scope of the disclosure is thereby intended. Various alterations, further modifications of the described embodiments, and any further applications of the principles of the disclosure, as described herein, are contemplated.

One illustrative embodiment of the present disclosure includes a system configured to select between a first sensor and a second sensor based on at least one of the position of a person on a person support surface, the pressure in support surface fluid bladders, a difference between the signal strength and/or clarity of the first sensor and a signal strength and/or clarity of a second sensor, and person support apparatus status information. Another illustrative embodiment includes a system configured to amplify and/or filter a signal from a first sensor as a function of at least one of a difference between the signal strength and/or clarity of the first sensor and a signal strength and/or clarity of a second sensor, the position of a person on a person support surface, the pressure in support surface fluid bladders, a comparison between a first sensor and second sensor, and person support apparatus status information.

A person support apparatus 1010 according to an illustrative embodiment of the current disclosure is shown in FIG. 1. The person support apparatus 10 includes a head section H1, where the head and a portion of the torso of a person (not shown) can be positioned, and a foot section F1, where the feet of a person (not shown) can be positioned. The person support apparatus 1010 includes a lower frame 1012 or base 1012, an upper frame 1014, a plurality of supports 1016, a fluid supply 1018, and a control system 1020. In some embodiments, the person support apparatus 1010 includes only one support 1016. The lower frame 1012 includes at least one lower frame section that is supported by casters 1022 as shown in FIG. 1.

The person support apparatus 1010 supports a person support surface 1024 or mattress 1024 on the upper frame 1014 as shown in FIGS. 1, 2, & 6-8. The person support surface 1024 is configured to support a person (not shown) in multiple articulated positions. The person support surface 1024 includes a back portion B1 and a main portion M1. The person support surface 1024 includes a cover 1026 or ticking 1026 that envelopes one or more support sections and/or layers having foam and/or fluid bladders 1028. The person support surface 1024 is configured to deliver therapy to the person, such as, for example, through sequential inflation/deflation of the fluid bladders 1028, rapid changes in pressure of the fluid in the fluid bladders 1028, and/or passing fluid through the person support surface 1024. For example, one or more portions of the surface 1024 provides alternating pressure therapy, continuous lateral rotation therapy, low air loss therapy, boost assistance, percussion/vibration therapy, and/or other therapies. In some contemplated embodiments, the person support surface 1024 includes a coverlet (not shown) that overlies another person support surface 1024 and that is configured to deliver therapy to a person supported thereon.

The supports 1016 are coupled with the upper frame 1014 and the lower frame 1012 and define a vertical axis Z1 that extends through the lower frame 1012 and the upper frame 1014 substantially perpendicular when the lower frame 1012 and the upper frame 1014 are parallel one another as shown in FIG. 1. In the illustrative example, the supports 1016 are lift mechanisms 1016 with a lift driver (not shown) that causes the lift mechanisms 1016 to expand and/or contract to raise and/or lower the upper frame 1014 with respect to the lower frame 1012. In some embodiments, the supports 1016 include at least one of telescoping towers, scissor lifts, rotational lifts, hydraulic lifts or actuators, pneumatic lifts or actuators, linear actuators, electronic actuators, chain lifts, or other lift mechanisms. In some embodiments, the supports 1016 comprise at least one fixed column (not shown). According to some embodiments, the supports 1016 move the upper frame 1014 to a Trendelenburg/reverse Trendelenburg position and/or rotate the upper frame 1014 from side to side with respect to the lower frame 1012.

Figure 3:
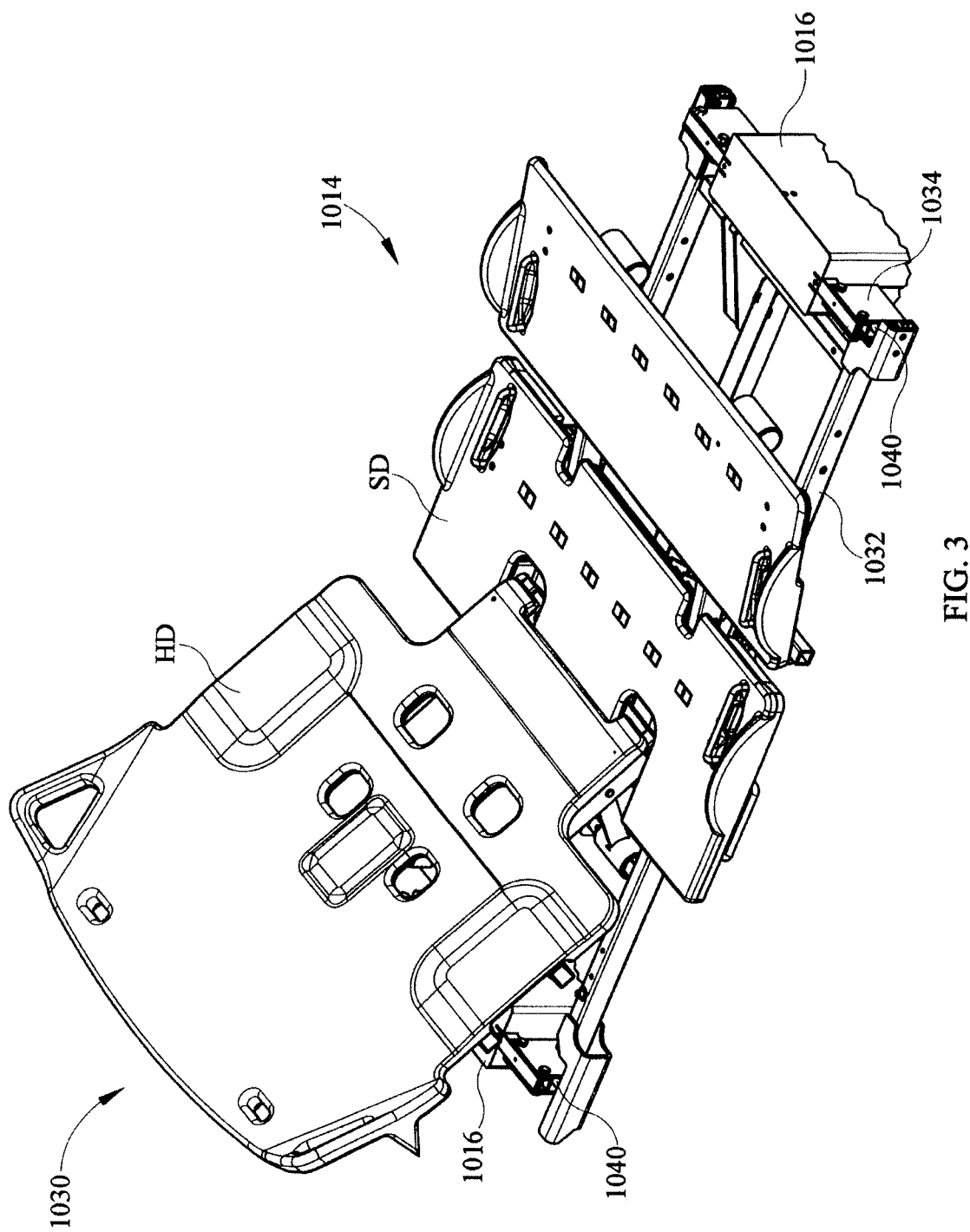
FIG. 3 is a perspective view of the upper frame according to one illustrative embodiment of the person support apparatus of FIG. 1.

The upper frame 1014 defines a longitudinal axis X1 that extends at least the length of the person support apparatus 1010 through the head end H1 and the foot end F1 along the lateral center of the upper frame 1014, and a lateral axis Y1 that is perpendicular to the longitudinal axis X1 and extends at least the width of the person support apparatus 1010 through the longitudinal center of the upper frame 1014 as shown in FIGS. 1 and 3. The upper frame 1014 includes a deck 1030, an intermediate frame 1032, and an upper frame base 1034 coupled to the supports 1016 which support the deck 1030 and the intermediate frame 1032. In some embodiments, the upper frame 1014 also includes a footboard FB, a head board HB, and/or siderails SR supported by the intermediate frame 1032. In some embodiments, the upper frame 1014 only includes a deck 1030. The deck 1030 has multiple sections, such as, a head deck section HD, a seat deck section SD, and a foot deck section FD, that are pivotably coupled to one another and/or the deck 1030 and articulate about the lateral axis Y1.

The fluid supply 1018 couples to the person support surface 1024 through a conduit C1 and is configured to supply fluid to the fluid bladders 1028 of the person surface 1024 as shown in FIG. 3. In some embodiments, the fluid supply 1018 also supplies fluid to the coverlet (not shown). In some embodiments, the fluid supply 1018 supplies gas to the person support surface 1024. The fluid supply 1018 includes a fluid source (not shown) such as an air blower (not shown) or an air compressor (not shown). The fluid supply 1018 includes a user interface (not shown) and/or a controller (not shown) that controls the operation of the fluid source in response to an input from a user or control system, such as, control system 1020.

Figure 5:
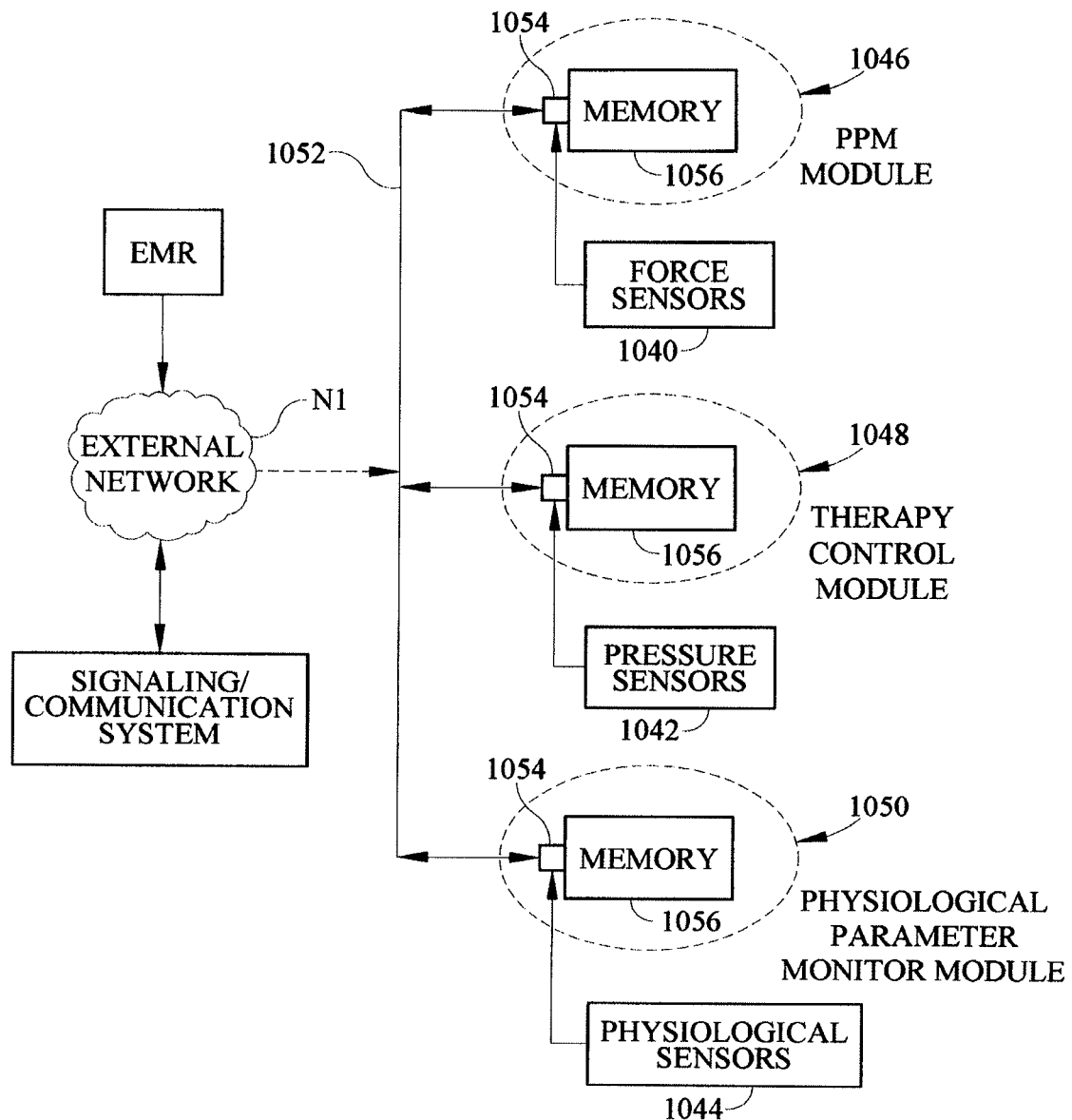
FIG. 5 is a diagrammatic view of a control system for the person support apparatus of FIG. 1 according to another illustrative embodiment.
Figure 6:
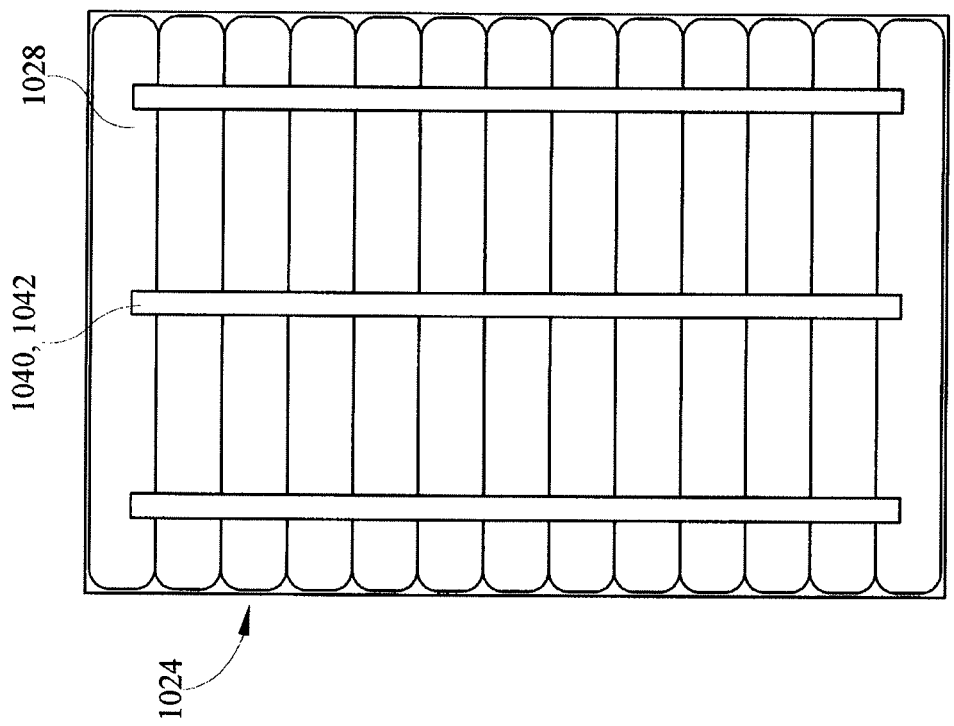
FIG. 6 is a top view of the fluid bladders within the person support surface of FIG. 2 with pressure sensors coupled across the bladders according to one illustrative embodiment.

The control system 1020 includes a plurality of sensors 1036 and control modules 1038 as shown in FIGS. 5 and 6. In some embodiments, the control system 1020 is configured to control various functions of the person support apparatus 1010 including, but not limited to, for example, articulating the deck 1030 with respect to the intermediate frame 1032, administering therapy to a person supported on the person support apparatus 1010, alerting caregivers when a person is exiting the person support apparatus 1010, alerting caregivers when a person is out of a desired position relative to the person support surface 1024, output information processed by the control system 1020 to a display (not shown), etc. The control system 1020 is coupled to the upper frame 1014 in some instances. In other instances, the control system 1020 is coupled to the lower frame 1012, supports 1016, a siderail, and/or elsewhere on the person support apparatus 1010. In further embodiments, the control system 1020 is incorporated within or coupled to the person support surface 1024. In some embodiments, the control modules 1038 are integrated into a graphical user interface (not shown). In other embodiments, the control system 1020 is integrated into an external network (not shown), such as, a hospital network, in communication with the person support apparatus 1010.

The sensors 1036 are operatively coupled to the control modules 1038 and are configured to sense various parameters, including, but not limited to, for example, a person's physiological information, a position of a person on the person support apparatus 1010 and/or person support surface 1024, a pressure of the fluid inside the bladders 1028 in the person support surface 1024, or other various parameters. In some embodiments, the sensors 1036 comprise force sensors 1040 that are coupled to the upper frame 1014 and that are configured to measure force on the upper frame 1014 as shown in FIGS. 5 and 6. In some embodiments, the sensors 1036 are force sensors 1040 that are configured to measure force on the upper frame 1014 and that are positioned between the intermediate frame 1032 and the upper frame base 1034 so as to couple the intermediate frame 1032 and deck 1030 to the upper frame base 1034.

Figure 2:
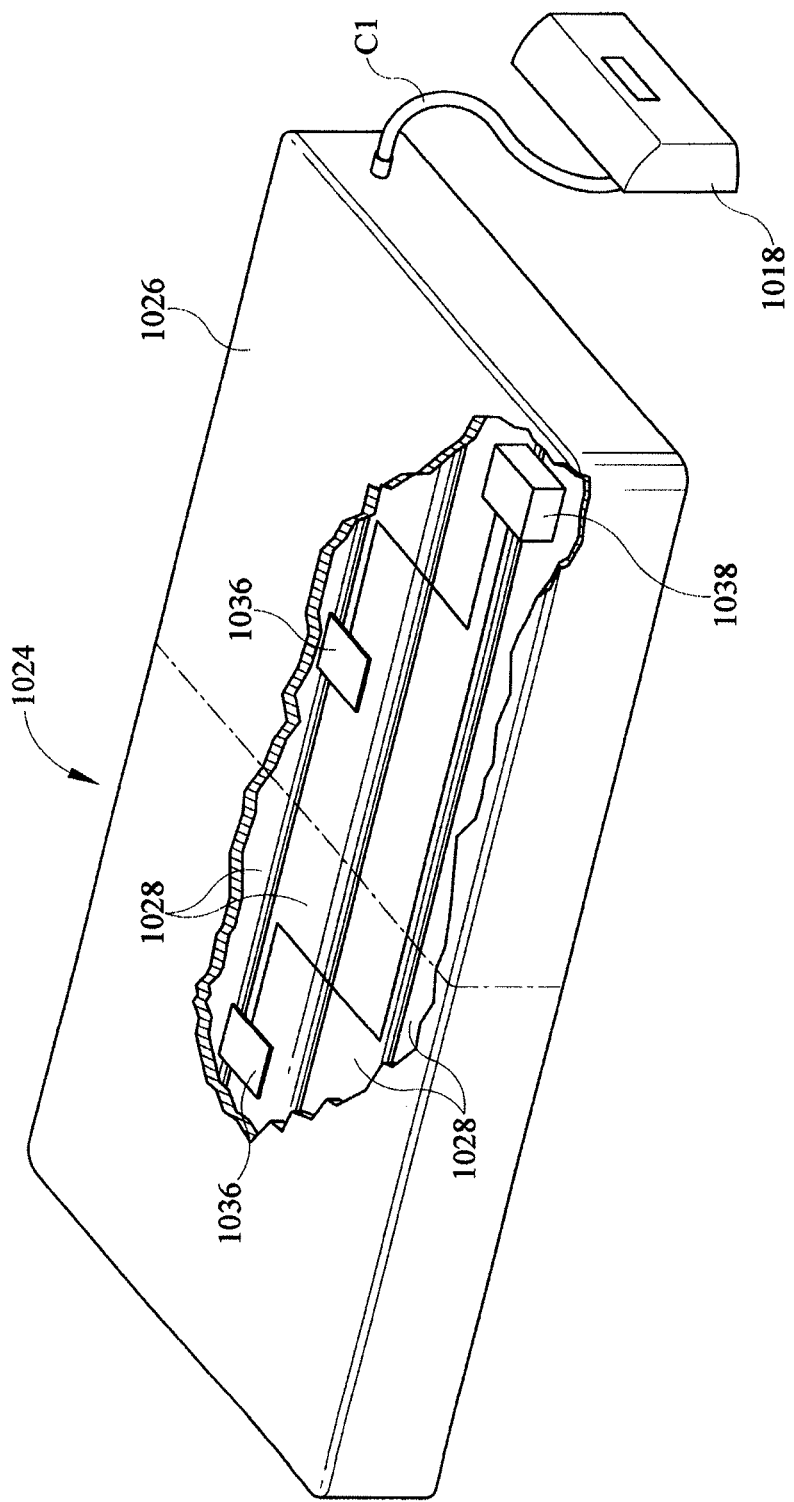
FIG. 2 is perspective view of the person support surface of FIG. 1 according to one illustrative embodiment partially cut away to reveal sensors integrated therein.

In some contemplated embodiments, the sensors 1036 are force sensors 1040 that are integrated into the person support surface 1024 and that are configured to measure changes in force on the person support surface 1024 as shown in FIG. 2. In some embodiments, the force sensors 1040 are coupled to the supports 1016 and/or the lower frame 1012. In further embodiments, the sensors 1036 are integrated into the casters 1022 and/or are engaged by the casters 1022. It is within the scope of this disclosure for the sensors 1036 to be integrated into the ticking 1026 such as being between the layers of the ticking 1026. In some embodiments, the force sensors 1040 are load cells 1040 that are coupled proximate the corners of the intermediate frame 1032. In some embodiments, the force sensors 1040 are piezoelectric sensors and/or elongated sensor strips or arrays. In other embodiments, the force sensors 1040 are other types of force sensors 1040 and are positioned in other locations on the upper frame 1014 and/or within the person support surface 1024.

Figure 7:
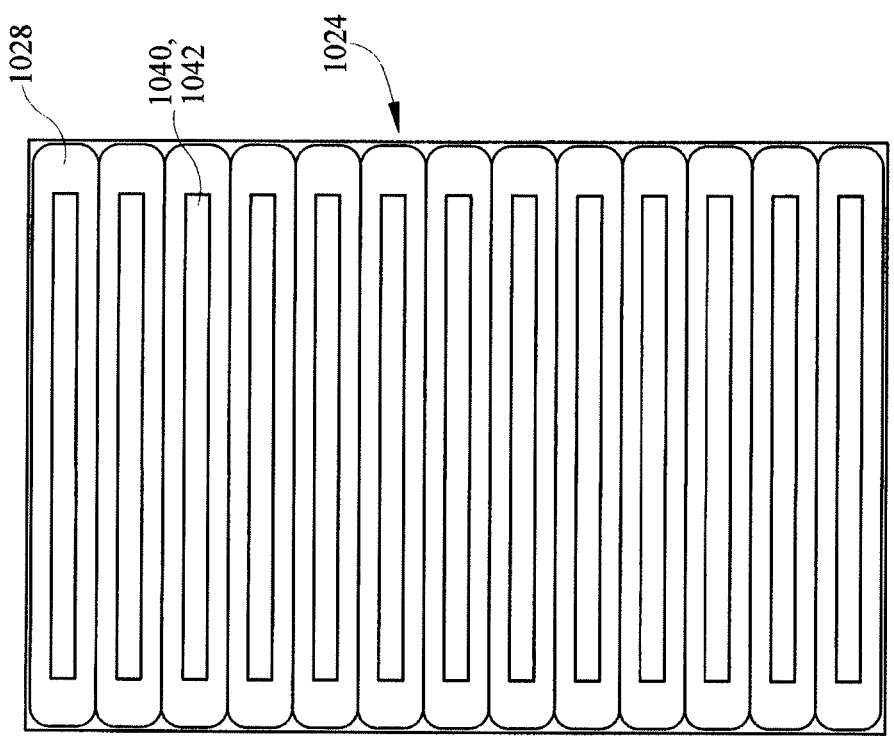
FIG. 7 is a top view of the fluid bladders within the person support surface of FIG. 2 with pressure sensors coupled along the bladders according to another illustrative embodiment.

In some embodiments, the sensors 1036 are pressure sensors 1042 that are integrated into the person support surface 1024 and that are configured to measure the pressure in/among the fluid bladders 1028 in the person support surface 1024 as shown in FIGS. 6-8. In some embodiments, the pressure sensors 1042 are coupled between the bladders 1028 such that they allow communication between adjacent bladders 1028. It some embodiments, the pressure sensors are situated within the bladders 1028 and measure the pressure within the bladder 1026.

In some embodiments according to this disclosure, the sensors 1036 are physiological sensors 1044 that are integrated into the person support surface 1024 and that are configured to measure one or more physiological parameters of a person supported on the person support surface 1024 as shown in FIG. 2. For example, one or more of the force sensors 1040 and one or more of the pressure sensors 1042 sense different physiological parameters in some embodiments. In some embodiments, the physiological sensors 1044 are used to sense the heart rate and/or respiration rate of a person supported on the person support surface 1024. Alternatively or additionally, oen or more of the physiological sensors 1044 sense the temperature of the person. It also contemplated by this disclosure for the physiological sensors 1044 to be configured to sense the movement and/or weight of the person on the person support surface 1024. In some embodiments, one or more of the physiological sensors 1044 are configured to sense the relative humidity of a tissue on the person support surface 1024. In some embodiments, the physiological sensors 1044 are pressure-strip sensors disposed on the fluid bladders 1028 along an axis parallel with the lateral axis Y1 and/or along an axis parallel with the longitudinal axis X1.

The control modules 1038 are each configured to perform different operations in the illustrative example. However, in some embodiments, a single control module 1038 is configured to perform the multiple different operations. In some embodiments, a single control module 1038 is configured to perform operations independently or in conjunction with at least one other control module 1038. In some embodiments, a first control module 1038, such as, a person position monitor module 1046 (PPM), is configured to detect the position of a person on the person support apparatus 1010. In some such embodiments, a second control module 1038, such as a therapy control module 1048, is configured to sense and/or modify the pressure within the fluid bladders 1028. In further such embodiments, a third control module 1038, such as a physiological parameter monitor module 1050, is configured to detect a person's physiological information.

Figure 4:
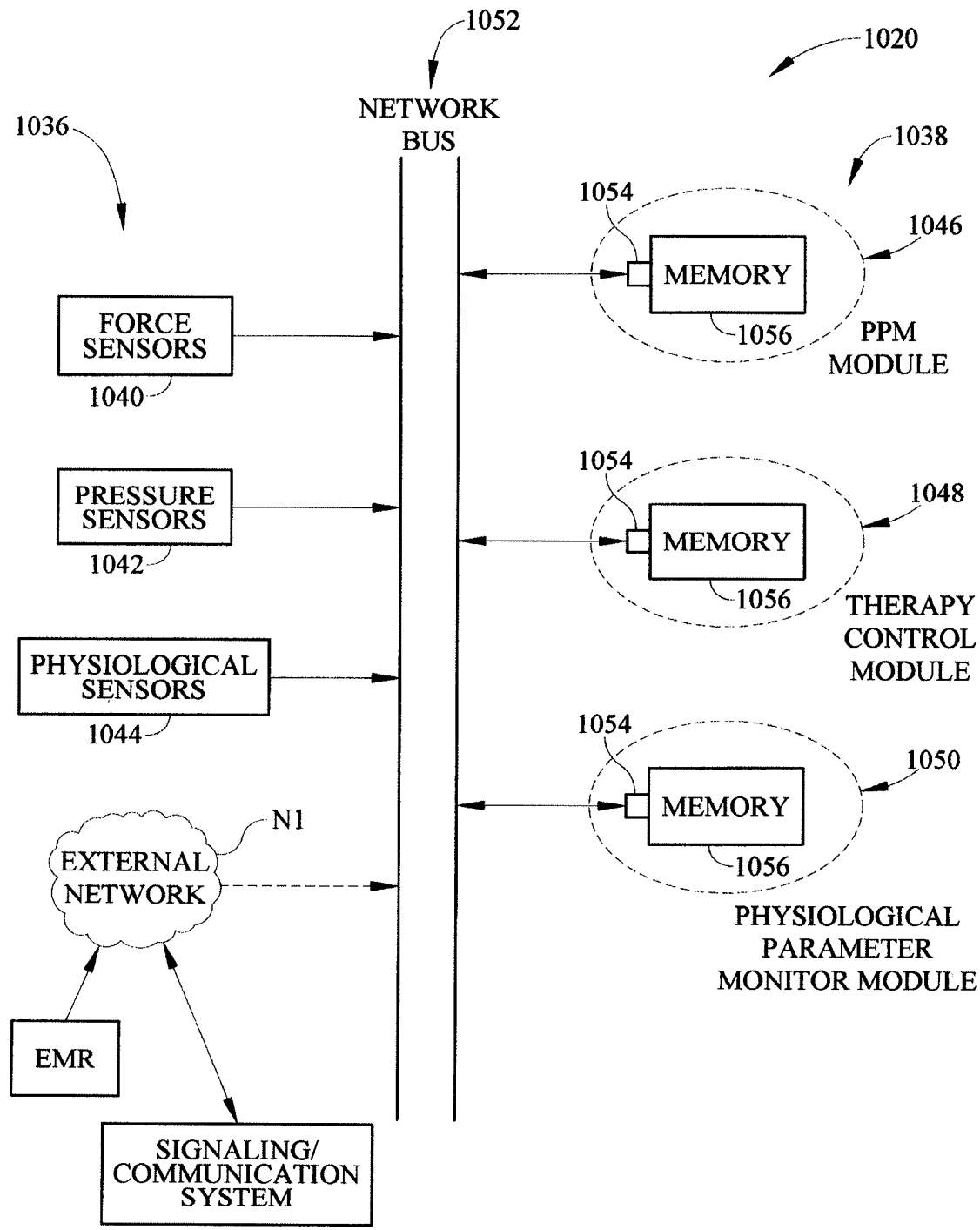
FIG. 4 is a diagrammatic view of a control system for the person support apparatus of FIG. 1 according to one illustrative embodiment.

In some embodiments, the control modules 1038 are operatively coupled together through a network 1052 as shown in FIGS. 4 and 5. The network 1052 facilitates communication between the various modules and/or equipment connected to the network 1052. In some embodiments, the network 1052 is a CAN network on a person-support apparatus 1010. Alternatively or additionally, the network 1052 comprises a hospital network (not shown). In some embodiments, the network 1052 includes other types of networks or communication protocols that facilitate communication between two or more devices. It is contemplated by this disclosure that the modules 1038 can be configured to connect to the network 1052 wirelessly, if desired. In some embodiments, the control modules 1038 negotiate with the network 1052 to be a network node. In some embodiments, the control modules 1038 are located at or on any node on the network 1052 and/or distributed across multiple nodes on the network 1052.

The control modules 1038 are implemented using software and/or hardware. In some embodiments, the control modules 1038 are implemented in software and are configured to perform one or more operations as shown in FIGS. 4 and 5. In some embodiments, the modules 1038 are configured to communicate via a memory mailbox where information from one module is sent to the memory address of a recipient module. In other embodiments, the software modules are configured to push information to a memory location, such as, a stack, that the control modules 1038 monitor or periodically check for information that the software modules subscribe to.

In some embodiments, the control modules 1038 are implemented using hardware. In some such embodiments, the control modules 1038 include a controller 1054 or processor 1054 and memory 1056 as shown in FIGS. 4 and 5. The controller 1054 is provided as a single component or a collection of operatively coupled components; and is comprised of digital circuitry, analog circuitry, or a hybrid combination of both of these types. When of a multicomponent form, controller 1054 has one or more components remotely located relative to the others in some instances. The controller 1054 includes, for example, multiple processing units arranged to operate independently, in a pipeline processing arrangement, in a parallel processing arrangement, and/or such different arrangement as would occur to those skilled in the art. In some embodiments, processor 1054 is a programmable microprocessing device of a solid-state, integrated circuit type that includes one or more processing units and memory. It is within the scope of this disclosure for the controller 1054 to include one or more signal conditioners, modulators, demodulators, Arithmetic Logic Units (ALUs), Central Processing Units (CPUs), limiters, oscillators, control clocks, amplifiers, signal conditioners, filters, format converters, communication ports, clamps, delay devices, memory devices, and/or different circuitry or functional components as would occur to those skilled in the art to perform the desired communications. In some embodiments, the controller 1054 includes a computer network interface to communicate among various system components and/or components not included in the depicted system, as desired. The listed examples are not intended to be an exhaustive list of structures that are within the scope of controller 1054, but are instead only a non-exhaustive list of such structures which can have substantial differences in the manner in which they are implemented and/or operate.

The controller 1054 is operatively coupled with the sensors 1036 and receives information from the sensors 1036. In some embodiments, one or more of the sensors 1036 are operatively coupled to the network 1052 and the controller 1054 receives the information from the sensors 1036 and outputs from other modules 1038 via the network 1052. In some embodiments, one or more of the sensors 1036 are configured to produce an analog data signal and are connected directly to the controller 1054. Alternatively or additionally, one or more of the sensors 1036 are configured to produce a digital data signal, e.g., a serial digital data signal, that is transmitted to the network 1052, e.g., a Serial Peripheral Interface (SPI) network 1052, to communicate with the controller 1054. The signals are stored in the memory 1056, which is operatively coupled with the controller 1054. In some embodiments, the memory 1056 is integrated into the controller 1054.

Figure 9:
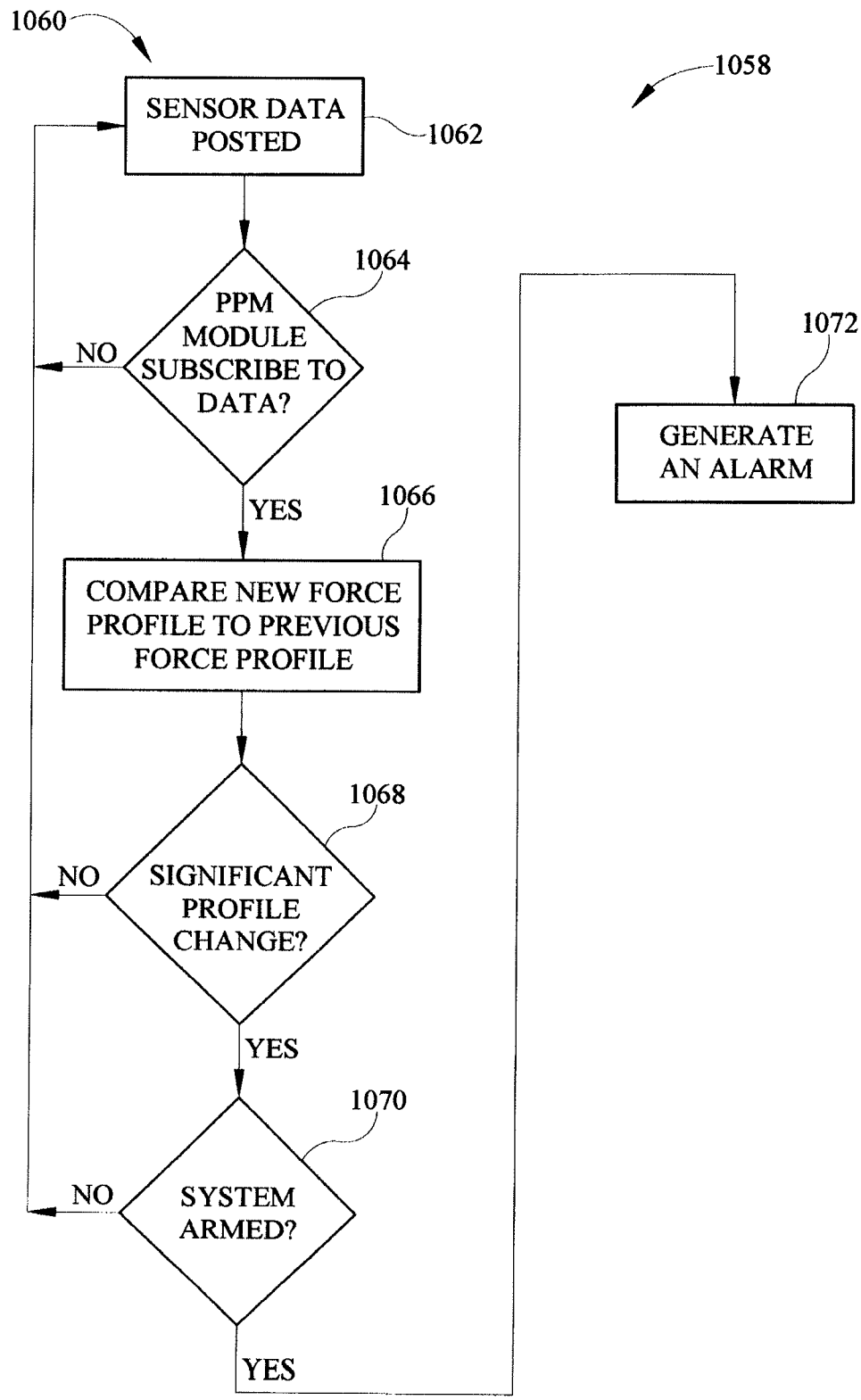
FIG. 9 is a flowchart for a procedure that can be executed by the control system of FIGS. 4 and/or 5 according to one illustrative embodiment.
Figure 12:
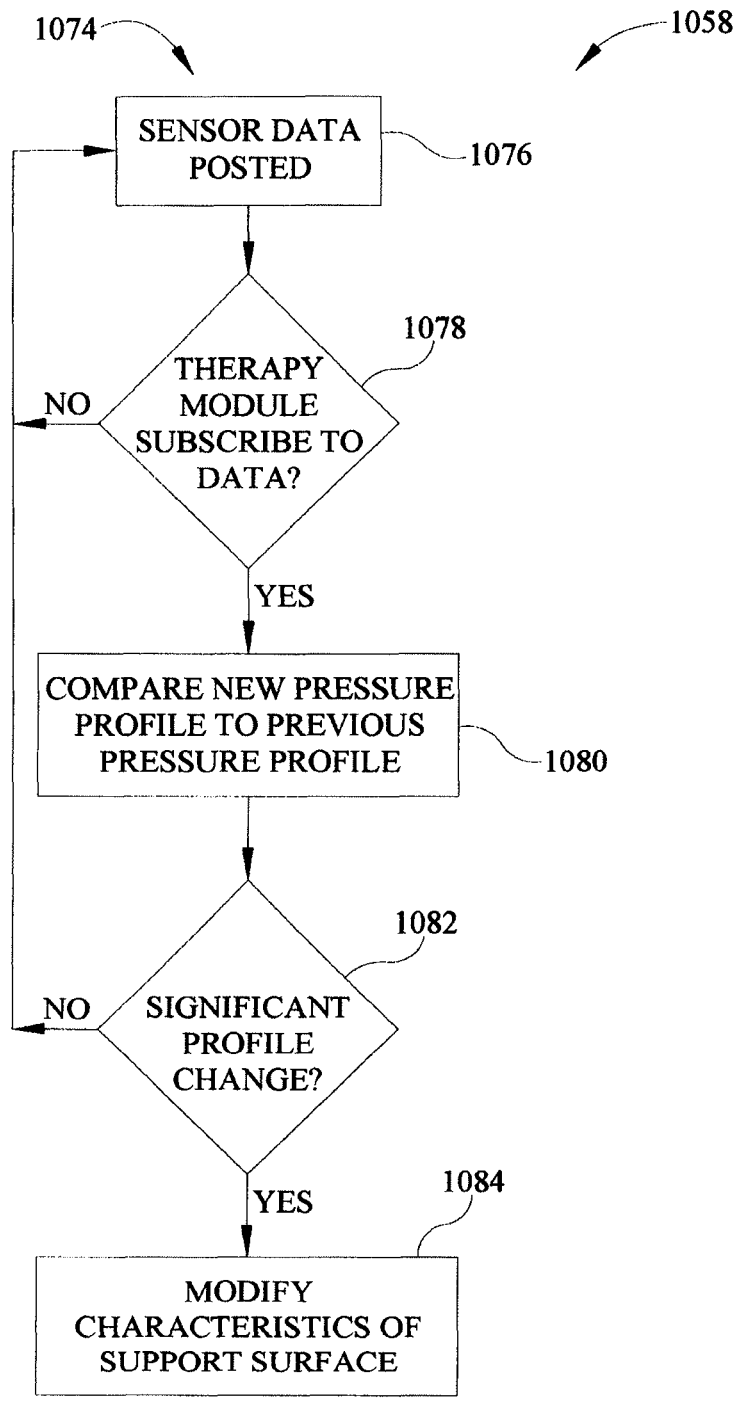
FIG. 12 is a flowchart for a procedure that can be executed by the control system of FIGS. 4 and/or 5 according to one illustrative embodiment.
Figure 13:
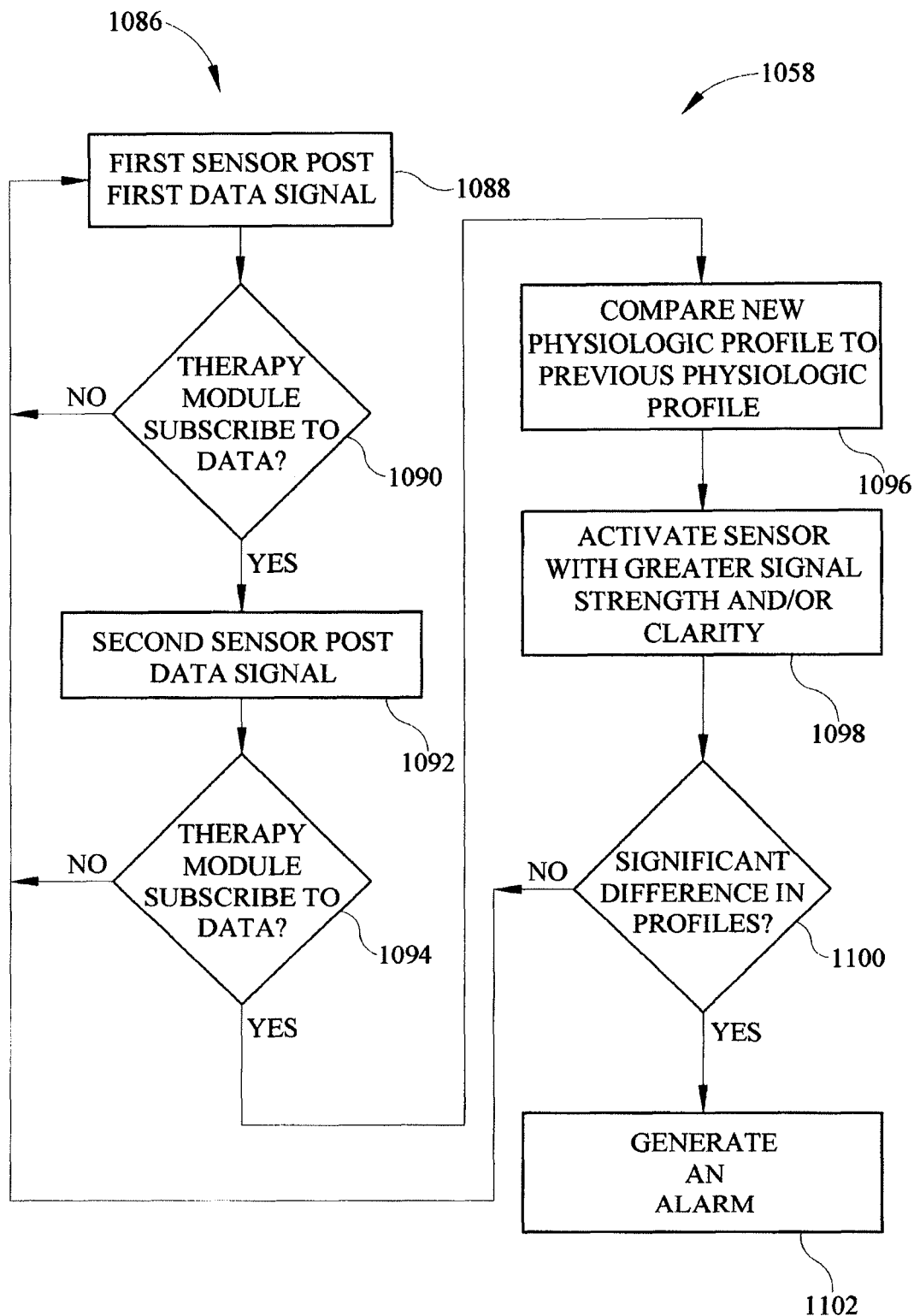
FIG. 13 is a flowchart for a procedure that can be executed by the control system of FIGS. 4 and/or 5 according to one illustrative embodiment.

The controller 1054 is configured to execute operating logic 1058 that defines various control, management, and/or regulation functions as shown in FIGS. 9, 12 and 13. In some embodiments, the software implemented modules include operating logic 1058. The operating logic 1058 is in the form of software, firmware, and/or dedicated hardware, such as, a series of programmed instructions, code, electronic files, or commands using general purpose or special purpose programming languages or programs executed on one or more general purpose or special purpose computers, processors, other control circuitry, or networks; a hardwired state machine; and/or a different form as would occur to those skilled in the art.

In some embodiments, one of the control modules 1038 is a patient position monitoring (PPM) module 1046. The memory 1056 of the controller 1054 includes operating logic 1058 with a number of software algorithms and other data that is executed by the controller 1054 to monitor patient movement relative to a reference load cell 1040 distribution, impending exit from the person support surface 1024 and/or exit therefrom. In some embodiments, the operating logic 1058 for managing such functions is in accordance with FIG. 5 in the form of a combined flowchart and/or state machine. The operating logic 1058 is executed periodically by the controller 1054, e.g., once every 200 ms, to monitor patient movement relative to a reference load cell 1040 distribution, impending exit from the mattress 1024 and/or exit from the mattress 1024. Referring to FIG. 5, the operating logic 1058 begins with the controller 1054 determining whether the person position monitor module 1046 is armed, i.e., whether one of the patient monitoring modes was active, before the last power down of the person position monitor module 1046.

The patient monitoring modes includes a patient movement (PM) mode wherein the person position monitor module 1046 is operable to monitor movement of a patient on the mattress 1024 by monitoring weight distribution among two or three of the four load cells 1040 relative to a predefined set of PM load cell threshold data, a patient exit (PE) mode wherein the person position monitor module 1046 is operable to monitor impending exit from the mattress 1024 by monitoring weight distribution of the four load cells 1040 relative to a predefined set of PE load cell threshold data, and a patient out-of-bed (OOB) mode wherein the person position monitor module 1046 is operable to monitor exit of the patient from the mattress 1024 by monitoring the patient weight distributed over the four load cells 1040 relative to an alined patient weight, wherein the armed weight corresponds to the patient weight distributed over the four load cells 1040 when the patient monitoring mode was armed as will be described in greater detail hereinafter. In any case, if the controller 1054 determines that the person position monitor module 1046 was not armed before the last system power down, execution of the operating logic 1058 causes the controller 1054 to execute a state machine preparation routine. If the controller 1054 instead determines that the person position monitor module 1046 was armed before the last system power down, execution of the operating logic 1058 advances to an Arming From Power Up Transition State of the state machine where the patient weight is processed to determine whether it is contained within a defined armed range prior to advancing to the PM Active State of the state machine to resume operation of the patient monitoring mode that was active at the last system power down. One example of such a system can be found in U.S. Pat. No. 7,253,366 to Bhai, issued on Aug. 7, 2007.

In some embodiments, the controller 1054 detects the ingress/egress of a person to/from the person-support apparatus 1010 by determining the center of gravity of the weight thereon. One example of such a system can be found in U.S. Pat. No. 5,276,432 to Travis, issued on Jan. 4, 1994. In still another illustrative embodiment, the controller 1054 treats the upper frame 1014 as though it were disposed within a horizontal plane, extracts from the weight value measured by each load cell 1040 a portion which represents the weight of a patient, uses the extracted portions to calculate the location within the plane of a center of gravity of the patient, determines whether the location of the center of gravity is inside or outside a predetermined region which is a portion of the plane, and initiates an alarm when it is found that the center of gravity is located outside the predetermined region. One example of such a system can be found in U.S. Pat. No. 5,276,432.

In some embodiments, the controller 1054 of the PPM module 1046 includes operating logic 1058 in the form of procedure 1060, for example, as shown in the flowchart of FIG. 9. Procedure 1060 includes operations/conditionals shown in blocks 1062, 1064, 1066, 1068, 1070, and 1072. Procedure 1060 evaluates changes in the force profile (FP) for the surface 1024 as a function of the difference between the last sensed force values (LSFV) and the newly sensed force values (NSFV) as represented by the following equation:

$$\Delta FP \begin{bmatrix} A & B \\ C & D \end{bmatrix} = LSFV \begin{bmatrix} A_L & B_L \\ C_L & D_L \end{bmatrix} - NSFV \begin{bmatrix} A_N & B_N \\ C_N & D_N \end{bmatrix}$$

Procedure 1060 begins with the operation of block 1062 where, in some embodiments, the force sensors 1040 post an electronic data signal representing at least one of an event and an amount of force on the network 1052. In some embodiments, the force sensors 1040 post data signals continuously and/or over at predetermined intervals. Alternatively or additionally, the force sensors 1040 post data signals in response to a query from a PPM module 1046. In some embodiments, the data signals include information that identifies what operations and/or control modules 1038 the data can be utilized by. It should also be appreciated that posting can mean sending data out on a network. In some embodiments, the sensors 1036 are operatively coupled directly to specific control modules 1038, for example, the force sensors 1040 being operatively coupled to the PPM module 1046, the pressure sensors 1042 being operatively coupled to a therapy control module 1048, and the physiological sensors 1044 being operatively coupled to a physiological parameter monitor module 1050.

In the conditional of block 1064, the PPM module 1046 examines the data signal posted by the force sensors 1040 on the network 1052 and determines whether or not the PPM module 1046 performs any operations that utilize the data as an input, i.e., whether or not the PPM module 1046 subscribes to the data signal. Other control modules 1038, such as, the therapy control module 1048 and/or the physiological parameter monitor module 1050, also subscribe to the force sensor 1040 data signal and receives the data as an input, while control modules 1038 that do not subscribe to the data disregard the data and wait for data signals to be posted that they do subscribe to.

In the operation of block 1066, the controller 1054 of the PPM module 1046 inputs the data into the control logic 1058 that utilizes the data as an input. In the PPM control logic 1058, the controller 1054 stores the posted data in the memory 1056 and compares previously posted data and newly input data to determine changes in the force profile of a person on the surface 1024, i.e., determine if and where a person has moved with respect to the surface 1024.

Figure 10:
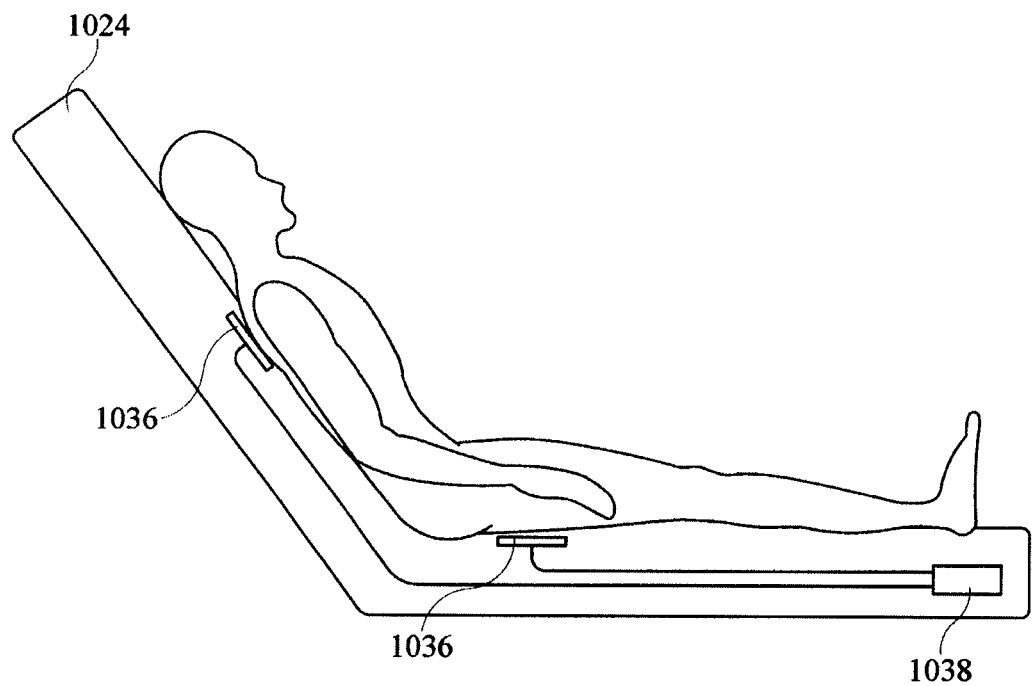
FIG. 10 is a partial diagrammatic view of a person in a first position with respect to the person support surface of FIG. 1 according to one illustrative embodiment.
Figure 11:
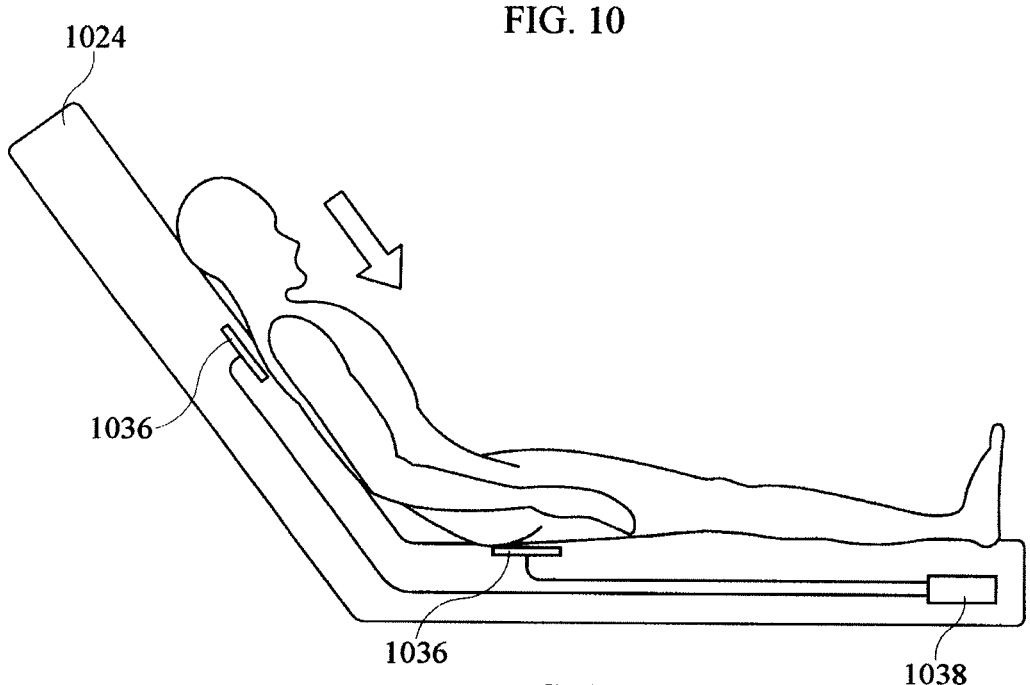
FIG. 11 is a partial diagrammatic view of a person in a second position with respect to the person support surface of FIG. 1.

In the conditional of block 1068, the controller 1054 determines if changes in the force profile are greater than a predetermined threshold. Changes in the force profile can potentially signify that the person is positioned higher on the surface 1024, i.e., more toward the head end H1 of the person support apparatus 1010, than desired; or that the person is positioned lower on the surface 1024, i.e., more toward the foot end F1 of the person support apparatus 1010, than desired. See FIGS. 10 and 11. In some embodiments, changes in the force profile is used to determine whether the person has moved to a side of the surface 1024 and/or how much they have moved with respect to the surface 1024. Such a determination is helpful in predicting whether the person is going to exit the person support apparatus 1010, adjusting the sensitivity of the sensors 1036 to compensate for movement, when a person is beginning to wake up, and/or whether continued therapy in the new/current position is desirable, or various other situations.

In the conditional of block 1070, if the controller 1054 determined in the conditional of block 1068 that the change in the force profile exceeded the predetermined threshold, the controller 1054 proceeds to determine whether or not the PPM system is armed, i.e., whether or not the PPM module 1046 is set to monitor the position of the person on the person support apparatus 1010. In some embodiments, a caregiver and/or the person on the person support apparatus 1010 activates and deactivates the PPM system locally through a caregiver interface on the person support apparatus 1010 or remotely. If the PPM system is armed, then the controller 1054 generates an alert signal in the operation of block 1072 to alert a caregiver that the person on the person support apparatus 1010 is about to exit the person support apparatus 1010. In some embodiments, the controller 1054 also communicates the amount the person has moved with respect to the person support apparatus 1010. The controller 1054 communicates the alert signal wirelessly or over a hospital network or an adverse condition alert system, such as, the Navicare® system sold by Hill-Rom Company, Inc., a caregiver station, a mobile paging device, a cellular phone, a pendant, over an intercom, or through other caregiver notification methods and devices. If the PPM system is not armed, then the controller 1054 returns to the operation of block 1062. In some embodiments, the controller 1054 generates signals representative of an event, e.g., the person has moved toward the head section H1, and/or an amount that the person has moved with respect to the person support apparatus 1010 and post the signals back on the network 1052 before returning to operation 1062 since other control modules 1038 can subscribe to the output of the PPM module 1046. In some embodiments, the controller 1054 prevents a user from accessing specific features on a user interface (not shown) based on the movement/positioning of the person on the person support surface 1024.

In some embodiments, one of the control modules 1038 is a therapy control module 1048. The therapy control module 1048 is operatively coupled to the pressure sensors 1042 and the fluid supply 1018. In some embodiments, the therapy control module 1048 controls various therapies that are administered to the person, such as, lateral rotation, percussion vibration, low air loss, or other therapies. The therapy control module 1048 includes operating logic 1058 in the form of procedure 1074, for example, as shown in the flowchart of FIG. 12. Procedure 1074 includes the operations/conditionals of blocks 1076, 1078, 1080, 1082, and 1084. Procedure 1074 evaluates changes in the pressure profile (PP) for the surface 1024 as a function of the difference between the last sensed pressure values (LSPV) and the newly sensed pressure values (NSPV) as represented by the following equation:

$$\Delta PP[P]=LSPV[P_L]-NSPV[P_N]$$

Procedure 1074 begins with the operation of block 1076 where, in some embodiments, the pressure sensors 1042 post an electronic data signal representing at least one of an event and an amount on the network 1052. In the conditional of block 1078, the therapy control module 1048 examines the data signal posted by the pressure sensors 1042 on the network 1052 and determines whether or not the therapy control module 1048 performs any operations that utilize the data as an input, i.e., whether or not the therapy control module 1048 subscribes to the data signal.

In the operation of block 1080, the controller 1054 of the therapy control module 1048 inputs the data into the control logic that utilizes the data as an input. In some embodiments, the controller 1054 of the therapy control module 1048 inputs the data into the therapy control logic 1058. In the therapy control logic 1058, the controller 1054 stores the posted data in the memory 1056 and compares previously posted data and newly input data to determine changes in the pressure profile of a person on the surface 1024, i.e., determine if, where, and by how much a person has moved with respect to the surface 1024.

In the conditional of block 1082, the controller 1054 determines if changes in the force profile are greater than a predetermined threshold. Changes in the pressure profile can potentially signify that the person is positioned higher on the surface 1024, i.e., more toward the head end H1 of the person support apparatus 1010, than desired; or that the person is positioned lower on the surface 1024, i.e., more toward the foot end F1 of the person support apparatus 1010, than desired. In some embodiments, changes in the pressure profile is used to determine whether the person has moved toward a side of the surface 1024 and/or how much they have moved with respect to the surface 1024. Such a determination is helpful in predicting whether the person is going to exit the person support apparatus 1010 and/or whether therapy in the current position or a new position is desirable.

In the operation of block 1084, if the controller 1054 determined in the conditional of block 1082 that the change in the force profile exceeded the predetermined threshold, the controller 1054 cooperates with the fluid supply 1018 to modify various characteristics of the support surface 1024. In some embodiments, the controller 1054 cooperates with the fluid supply 1018 to adjust the pressure of the fluid within the fluid bladders 1028 as a function of the movement. In some embodiments, the pressure in the fluid bladders 1028 is changed to maintain a comfort level of a person by reducing the pressure in some bladders 1028 and increasing the pressure in other bladders 1028 to compensate for the movement of the person. In some embodiments, the controller 1054 cooperates with the fluid supply 1018 to adjust a therapy, such as, continuous lateral rotation, percussion vibration, or other therapies, as a function of the movement. In some embodiments, the therapy is stopped completely or at least until the person moves back to within a predetermined range of the previous position. In some embodiments, the controller 1054 generates signals representative of an event, e.g., the pressure profile has changed, which can potentially signify movement of the person with respect to the surface 1024, and/or an amount that the pressure has increased, or an amount the pressure profile has changed and post the signals back on the network 1052 before returning to operation 1076, since other control modules 1038 subscribe to the output of therapy control module 1048 in some instances.

In some embodiments, one or more of the control modules 1038 are a physiological parameter monitor module 1050. The physiological parameter monitor module 1050 is operatively coupled with the physiological sensors 1044. The physiological parameter monitor module 1050 includes operating logic 1058 in the form of procedure 1086. In some embodiments, procedure 1086 evaluates changes in the physiological sensor signal strength and/or clarity (PS) for the surface 1024 to determine whether a first physiological sensor 1044 would provide a more desirable signal and should be used instead of a second physiological sensor 1044. Thus, according to this disclosure, one or more of some sensors 1044 are turned on and one or more of others are turned off depending upon which sensors have or are expected to have the best quality data signals. Information from the PPM system of the person support apparatus, for example, may be used to determine that the sensors 1044 on the left half of the apparatus should be turned on and the sensors on the right half 1044 should be turned off based on the position of the patient being more toward the left half of the apparatus, or vice versa. Other subsets of the sensors may be turned on and off in other scenarios such as, for example, turning on sensors in a seat section if the PPM system indicates that the patient is likely sitting up while turning off sensors in zones or sections of the person support apparatus that are no longer supporting a person.

In some embodiments, procedure 1086 evaluates the changes in the PS as a function of the difference between a first physiological sensor signal strength and/or clarity (FPS) and a second physiological sensor signal strength and/or clarity (SPS) as represented by the following equation:

$$\Delta PS[S] = FPS[S_L] - SPS[S_N]$$

In other embodiments, procedure 1086 subscribes to data on the network 1052 and uses the data to determine what sensor 1036 or sensor array 1036, i.e., physiological sensor 1044 or sensor array 1044, should be activated or turned on to obtain the most desirable physiological signal. In some embodiments, procedure 1086 subscribes to output signals from the PPM module 1046 regarding the position of the person with respect to the surface 1024 and causes the physiological parameter monitor module 1050 to activate and/or receive input signals from different sensors 1036 as a function of the position of the person. In some embodiments, procedure 1086 subscribes to data on the network 1052 corresponding to the angle of articulation of the head deck section HD and causes the physiological parameter monitor module 1050 to activate and/or receive input signals from different sensors 1036 as a function of the angle of articulation of the head deck section HD. For example, depending upon the angle of articulation of the head deck section HD, the physiological parameter monitor module 1050 activates and/or receives input signals from a first sensor when the angle of articulation of the head deck section HD is less than a first angle and activates and/or receives input signals from a second sensor when the angle of articulation of the head deck section HD is greater than or equal to a second angle. In some embodiments, the angle is about 30°.

According to this disclosure, procedure 1086 includes the operations/conditionals of blocks 1088, 1090, 1092, 1094, 1096, and 1098 as shown in the flowchart of FIG. 13. Procedure 1086 begins with operation 1088 where, in some embodiments, a first physiological sensor 1044 posts an electronic data signal representing at least one of an event and an amount on the network 1052. In the conditional of block 1090, the controller 1054 examines the data signal posted by a first physiological sensor 1044 and determines whether or not the physiological parameter monitor module 1050 performs any operations that utilize the data as an input, i.e., whether or not the physiological parameter monitor module 1050 subscribes to the data signal. If the controller determines that the module 1050 subscribes to the data, the first signal is stored in the memory 1056.

In the operation of block 1092, the controller 1054 deactivates the first physiological sensor 1044 and activates a second physiological sensor 1044. In some instances, the first physiological sensor 1044 and the second physiological sensor 1044 can both be active. Deactivating or turning off a sensor within the scope of this disclosure includes at least one of receiving information from the sensor but not using it, blocking and/or breaking communication with the sensor, and/or cutting power to the sensor. The second physiological sensor 1044 posts an electronic data signal representing at least one of an event and an amount on the network 1052 in some instances.

In the conditional of block 1094, the controller 1054 examines the data signal posted by a second physiological sensor 1044 and determines whether or not the physiological parameter monitor module 1050 subscribes to the data signal. If the controller 1054 determines that the module 1050 subscribes to the data, the first signal is stored in the memory 1056. In the conditional of block 1096, the controller 1054 compares the first sensed signal with the second sensed signal.

In the operation of block 1098, if the controller 1054 determines that the signal from the first physiological sensor 1044 has a higher signal strength, i.e., amplitude, and/or clarity than the signal generated by the second physiological sensor 1044, the controller deactivates the second physiological sensor 1044 and re-activate the first physiological sensor 1044. In some instances, both physiological sensors 1044 are simultaneously active. If the controller 1054 determines that the signal from the first physiological sensor 1044 has a lower signal strength and/or clarity than the signal generated by the second physiological sensor 1044, the controller 1054 continues to receive signals from the second physiological sensor 1044 in some embodiments. In some embodiments, if the controller 1054 determines that the signal from the first physiological sensor 1044 has a lower signal strength and/or clarity than the signal generated by the second physiological sensor 1044, the controller 1054 amplifies and/or filters the signal generated by the first physiological sensor 1044 to increase the signal strength and/or clarity of the first physiological sensor 1044.

In the conditional of block 1100, the controller determines if the difference between the first physiological sensor signal strength and/or clarity and the second physiological sensor signal strength and/or clarity is greater than a predetermined threshold. If the difference is greater than the predetermined threshold, then the controller 1054 generates an alert signal in operation 1102 to alert a caregiver. In some embodiments, the controller 1054 also communicates the value of the physiological sensor 1044 and posts back the value on the network 1052. In some embodiments, the controller 1054 communicates the alert signal wirelessly or over a hospital network or an adverse condition alert system, such as, the Navicare® system sold by Hill-Rom Company, Inc., a caregiver station, a mobile paging device, a cellular phone, a pendant, over an intercom, or through other caregiver notification methods and devices. If the difference between the first physiological sensor signal strength and/or clarity and the second physiological sensor signal strength and/or clarity is not significant, then the controller 1054 returns to the operation of block 1088.

In some embodiments, the controller 1054 generates signals representative of the difference between the first physiological sensor signal strength and/or clarity and the second physiological sensor signal strength and/or clarity and posts the signals back on the network 1052 before returning to the operation of block 1088 because other control modules 1038 subscribe to the output of the physiological parameter monitor module 1050 in some instances. In some embodiments, the controller 1054 prevents a user from accessing specific features on a user interface (not shown) based on the first physiological sensor signal strength and/or clarity and the second physiological sensor signal strength and/or clarity of the person on the person support surface 1024.

As mentioned above, the sensitivity of a signal form a sensor, such as sensors 1040, 1042, 1044, is adjusted to improve its signal strength and/or clarity. One way of accomplishing this is to change the gain of the sensor 1040, 1042, 1044. One gain change technique is to use switches, such as transistors or micro-switches to selectively open circuit or close circuit various parallel resistors in a feedback loop of a respective operational amplifier circuit to which signals from sensors 1040, 1042, 1044 are input. Thus, the operational amplifier circuit in such embodiments is considered to be part of the sensor. Use of transistors or micro-switches that are selectively activated or deactivated to couple the signals from sensors 1040, 1042, 1044 to one or more filters, such as a high pass filter, a low pass filter and/or a band pass filter is also contemplated by this disclosure. Digital signal processors that are programmable to implement one or more high pass filters, low pass filters, and/or band pass filters are also within the scope of this disclosure.

According to this disclosure, sensors that are included in person support apparatus 1010 and that have gain change and filtering capabilities associated therewith include moisture sensors, acoustic sensors, flow rate sensors, temperature sensors, force sensors, and pressure sensors, just to name a few. The frequency or frequencies that are filtered out from the signals of sensors 1040, 1042, 1044 include, for example, those associated with a motor that moves one portion of apparatus 1010 relative to another portion (e.g., deck articulation motors, such as linear actuators, or lift system motors), those associated with components of a pneumatic system of apparatus 1010 (e.g., blowers or compressors used to inflate mattress 1024), those associated with room ventilation equipment or fans, those associated with mechanical noise (e.g., bearing noise curing deck articulation), and those associated with separate medical equipment such as patient ventilators, IV pumps, passive motion machines, and the like.

In some embodiments, control system 1020 of apparatus 1010 receives information from a remote computer, such a computer associated with an electronic medical records (EMR) system to determine what types of separate medical equipment is being used with a particular person. Based on that information, system 1020 determines the appropriate frequency or frequencies to filter out from the signals from one or more of sensors 1040, 1042, 1044. A look-up table, for example, is provided in memory of control system 1020 with a list of "noise" frequencies associated with various types of medical equipment that are commonly used with persons to be supported on apparatus 1010. Alternatively or additionally, system 1020 performs its own analysis of signals from sensors 1040, 1042, 1044 before and after a particular component or piece of equipment starts operating or running and then determines the frequency or frequencies of the noise introduced into the signal as a result of the operation of the component or equipment. Thereafter, the appropriate frequency or frequencies is/are filtered out of the signals from sensors 1040, 1042, 1044. Alternatively or additionally, system 1020 adjusts the threshold criteria for sending alerts to caregivers depending upon whether particular components or pieces of equipment are being used.

In some embodiments, the control system 1020 is configured to change its operational characteristics based on the status of the person-support apparatus 1010 and/or the status of devices (not shown) coupled to the person-support apparatus 1010 and/or coupled to the person supported on the person-support apparatus 1010. In one example, the controller 1054 receives an input indicative that the angle of the head section of the deck has changed. In this example, the controller 1054 is configured to stop receiving input signals from a sensor coupled to the head section and start receiving signals from a sensor in the seat section, apply various filters, such as, band-pass, low-pass, and/or high-pass filters, to the input signal to eliminate undesired noise, or increases/ decreases the gain of the sensor as a function of the angle of the head section. In some instances, the sensor coupled to the head section is deactivated and the sensor in the seat section is activated. In some embodiments, the controller looks up a device in a look-up table and/or compares the signal prior to a change in status of the signal with the signal after the change in status to determine what noise the change in status might have introduced into the signal to determine the appropriate filter(s) to apply.

In another example, the controller 1054 receives an input indicative that continuous lateral rotation therapy is being administered by the person support apparatus 1010. Continuous lateral rotation therapy is used to rotate an occupant side to side to help reduce the risk of developing pressure ulcers. In some embodiments, continuous lateral rotation is implemented through the inflation and/or deflation of fluid bladders in the mattress and/or by rotating the upper frame about the longitudinal axis X1. In this example, the controller 1054 is configured to stop receiving input signals from a sensor coupled to one of the lateral sides of the person-support apparatus and start receiving signals from a sensor coupled to the other of the lateral sides of the person-support apparatus, apply various filters, such as, band-pass, low-pass, and/or high-pass filters, to the input signal to eliminate undesired noise, and/or increase/decrease the gain of the sensor as a function of the lateral rotation. Thus, the sensor coupled to or adjacent one of the lateral sides is deactivated and the sensor coupled to or adjacent the other of the lateral sides is activated. According to this disclosure, the activation/deactivation, filtering, and/or gain increase/decrease is applied to individual sensors in an array of sensors where more than one sensor is communicating signals to the controller.

In another example, the controller 1054 receives an input indicative of the status of a device coupled to the person-support apparatus and/or the person on the person-support apparatus. The information that another device is coupled to the person and/or person-support apparatus is sometimes available from the EMR or is sometimes input by a caregiver. In some instances, the device is in electronic communication, such as wireless or wired communication, with the person support apparatus 1010. In this example, the controller 1054 is configured to apply various filters, such as, band-pass, low-pass, and/or high-pass filters, to the input signal to eliminate undesired noise and/or change the gain of the sensors as a function of the device. As mentioned above, the controller looks up the needed information concerning the device in a look-up table and/or compares the signal prior to change in status with the signal after the change in status to determine what noise the change in status might have introduced to the signal to determine the appropriate filter(s) to apply. The controller 1054 also adjusts the parameters for any alarms that have been activated on the person-support apparatus, such as, PPM. In some embodiments, the controller 1054 modifies the operation of a single sensor or individual sensors in an array of sensors.

Any theory, mechanism of operation, proof, or finding stated herein is meant to further enhance understanding of principles of the present disclosure and is not intended to make the present disclosure in any way dependent upon such theory, mechanism of operation, illustrative embodiment, proof, or finding. It should be understood that while the use of the word preferable, preferably or preferred in the description above indicates that the feature so described can be more desirable, it nonetheless can not be necessary and embodiments lacking the same can be contemplated as within the scope of the disclosure, that scope being defined by the claims that follow.

In reading the claims it is intended that when words such as "a," "an," "at least one," "at least a portion" are used there is no intention to limit the claim to only one item unless specifically stated to the contrary in the claim. When the language "at least a portion" and/or "a portion" is used the item can include a portion and/or the entire item unless specifically stated to the contrary.

While embodiments of the disclosure have been illustrated and described in detail in the drawings and foregoing description, the same are to be considered as illustrative and not restrictive in character, it being understood that only the selected embodiments have been shown and described and that all changes, modifications and equivalents that come within the spirit of the disclosure as defined herein or by any of the following claims are desired to be protected.

The invention claimed is:

1. A patient support apparatus comprising
a lower frame,
an upper frame adjustable relative to the lower frame and comprising a support deck having a head deck section,
a vital signs sensor coupled to the head deck section and configured to detect at least one of heart rate and respiration rate,
at least one load sensor configured to detect a patient supported by the support deck,
a controller configured to control movements of the upper frame and the support deck, the controller being communicatively coupled to the vital signs sensor and the load sensor, and
a network communication interface coupled to the controller and configured to communicate data from the patient support apparatus to a remote electronic system, the data including vital signs information based on at least one signal from the vital signs sensor and patient weight information based on at least one signal from the at least one load sensor.

2. The patient support apparatus of claim 1, further comprising a pressure sensor configured to detect the pressure of an inflatable bladder.

3. The patient support apparatus of claim 1, wherein the controller is operable to adjust a sensitivity of the vital signs sensor.

4. The patient support apparatus of claim 3, wherein the controller is operable to adjust the sensitivity of the vital signs sensor in response to information from the at least one load sensor.

5. The patient support apparatus of claim 3, wherein the controller is operable to adjust the sensitivity of the vital signs sensor by changing a gain of the vital signs sensor or by changing a manner in which a signal from the vital signs sensor is filtered.

6. The patient support apparatus of claim 1, wherein the controller is operable to turn power to the vital signs sensor on and off.

7. The patient support apparatus of claim 6, wherein the controller is operable to turn power to the vital signs sensor on and off in response to information from the at least one load sensor such that power to the vital signs sensor is turned on by the controller in response to the at least one load sensor sensing that the patient is present on the patient support apparatus and such that power to the vital signs sensor is turned off by the controller in response to the at least one load sensor sensing that the patient is absent from the patient support apparatus.

8. The patient support apparatus of claim 1, further comprising a user interface coupled to the controller and configured to display information regarding the patient support apparatus.

9. The patient support apparatus of claim 1, wherein the controller is included as part of a controller area network (CAN) of the patient support apparatus.

10. The patient support apparatus of claim 1, wherein the controller is operable to monitor patient movement on the patient support apparatus based on signals from the at least one load sensor.

11. The patient support apparatus of claim 1, wherein the controller is operable to generate an alarm in response to the patient movement exceeding a threshold amount of movement.

12. The patient support apparatus of claim 10, wherein the controller is operable to generate an alarm in response to the patient movement indicating impending exit from the patient support apparatus.

13. The patient support apparatus of claim 10, wherein the controller is operable to generate an alarm in response to the patient exiting the patient support apparatus.

14. The patient support apparatus of claim 10, wherein the at least one load sensor comprises four load sensors that are coupled proximate corners of the upper frame.

15. The patient support apparatus of claim 10, wherein the controller is operable to filter out noise associated with separate medical equipment in a patient's room based on information received from an electronic medical record (EMR) system.

16. The patient support apparatus of claim 1, wherein the controller is operable to filter out noise associated with separate medical equipment in a patient's room based on information received from an electronic medical record (EMR) system.

17. The patient support apparatus of claim 1, wherein the controller is operable to implement via software at least one of a high pass filter, a low pass filter, and a band pass filter.

18. The patient support apparatus of claim 1, wherein the controller is operable to filter out noise associated with at least one electric component of the patient support apparatus.

19. The patient support apparatus of claim 1, wherein the controller is operable to filter out noise associated with at least one of a first electric component associated with the support deck and a second electric component associated with the upper frame.

20. The patient support apparatus of claim 1, further comprising telescoping towers supporting the upper frame relative to the lower frame and operable to adjust a height of the upper frame relative to the lower frame.

* * * * *